US011556742B2

(12) United States Patent
Levanony et al.

(10) Patent No.: US 11,556,742 B2
(45) Date of Patent: Jan. 17, 2023

(54) TRAINING MACHINE LEARNING MODELS TO EXCLUDE AMBIGUOUS DATA SAMPLES

(71) Applicant: International Business Machines Corporation, Armonk, NY (US)

(72) Inventors: Dana Levanony, Tel Aviv (IL); Tal Tlusty Shapiro, Zichon Yaacov (IL)

(73) Assignee: International Business Machines Corporation, Armonk, NY (US)

( * ) Notice: Subject to any disclaimer, the term of this patent is extended or adjusted under 35 U.S.C. 154(b) by 298 days.

(21) Appl. No.: 16/983,161

(22) Filed: Aug. 3, 2020

(65) Prior Publication Data
US 2022/0036128 A1 Feb. 3, 2022

(51) Int. Cl.
*G06K 9/62* (2022.01)
*G06N 20/00* (2019.01)
*G16H 30/20* (2018.01)

(52) U.S. Cl.
CPC ......... *G06K 9/6256* (2013.01); *G06K 9/6262* (2013.01); *G06K 9/6267* (2013.01); *G06N 20/00* (2019.01); *G16H 30/20* (2018.01); *G06V 2201/03* (2022.01)

(58) Field of Classification Search
CPC ...... G06K 9/62; G06K 9/6256; G06K 9/6262; G06K 9/6267; G06N 20/00; G16H 30/20
See application file for complete search history.

(56) References Cited

U.S. PATENT DOCUMENTS

| 2004/0151358 A1* | 8/2004 | Yanagita | G06T 7/0012 |
| | | | 382/132 |
| 2018/0259608 A1* | 9/2018 | Golden | G06N 3/02 |
| 2020/0184278 A1* | 6/2020 | Zadeh | G06K 9/6264 |

OTHER PUBLICATIONS

Amiri, et al., "Spotting Spurious Data with Neural Networks", Proceedings of NAACL-HLT 2018, pp. 2006-2016, <https://www.aclweb.org/anthology/N18-1182.pdf>.
Goldberger, et al., "Training Deep Neural-Networks Using a Noise Adaptation Layer", ICLR 2017 Conference Submission, Nov. 4, 2016, <https://openreview.net/forum?id=H12GRgcxg>.
Han, et al., "Co-teaching: Robust Training of Deep Neural Networks with Extremely Noisy Labels", 32nd Conference on Neural Information Processing Systems (NIPS 2018), Oct. 30, 2018, 13 pages, <https://arxiv.org/abs/1804.06872>.

(Continued)

*Primary Examiner* — Tuan H Nguyen
(74) *Attorney, Agent, or Firm* — Stephanie L. Carusillo (57) ABSTRACT

Techniques for training machine learning models for improved accuracy at classifying medical imaging data sets by trimming ambiguous samples from training data sets are described herein. In some embodiments, a machine learning model is trained using a data set, where a subset of the data set comprises data with a conflict between a first label based on an expert opinion and a second label based on a ground truth based on a medical examination. During some epochs of training the machine learning model, loss values for each data sample in the epoch are compared against a loss threshold, with data samples with corresponding loss values that exceed the loss threshold that also belong to the subclass trimmed from the data set for subsequent epochs of training. The loss threshold for the next epoch is then updated based on loss values of the trimmed data set.

18 Claims, 7 Drawing Sheets

(56) References Cited

OTHER PUBLICATIONS

Jin, et al., "Unsupervised Hard Example Mining from Videos for Improved Object Detection", Proceedings of the European Conference on Computer Vision (ECCV), Aug. 13, 2018, 18 pages, <https://arxiv.org/abs/1808.04285>.

Kendall, Edward, "Automatic detection of anomalies in screening mammograms", BMC Medical Imaging, Dec. 2013, 24 pages, <https://www.researchgate.net/publication/259316033>.

Li, et al., "Learning from Noisy Labels with Distillation", Proceedings of the IEEE International Conference on Computer Vision, Apr. 7, 2017, 9 pages, <https://arxiv.org/abs/1703.02391>.

Lin, et al., "Focal Loss for Dense Object Detection", arXiv:1708.02002v2, Feb. 7, 2018, 10 pages, <https://arxiv.org/abs/1708.02002>.

Nguyen, et al., "Robust Learning under Label Noise with Iterative Noise-Filtering", removarXiv:1906.00216v1, [cs.LG], Jun. 1, 2019, <https://arxiv.org/abs/1906.00216>.

Nguyen, et al., "Self: Learning To Filter Noisy Labels With Self-Ensembling", ICLR 2020 Conference, Mar. 16, 2020, 16 pages, <https://openreview.net/forum?id=HkgsPhNYPS>.

Patrini, et al., "Making Deep Neural Networks Robust to Label Noise: a Loss Correction Approach", arXiv:1609 03683v2, [stat.ML], Mar. 22, 2017, 9 pages <https://arxiv.org/abs/1609.03683>.

Ren, et al., "Learning to reweight examples for robust deep learning", Proceedings of the 35th International Conference on Machine Learning, PMLR 80, 2018, 13 pages, <https://arxiv.org/abs/1803.09050>.

Shen, et al., "Learning with Bad Training Data via Iterative Trimmed Loss Minimization", Proceedings of the 36th International Conference on Machine Learning, PMLR 97, 2019, 10 pages, <http://proceedings.mlr.press/v97/shen19e/shen19e.pdf>.

Shrivastava, et al., "Training Region-based Object Detectors with Online Hard Example Mining", arXiv:1604.03540v1, Apr. 12, 2016, 9 pages, <https://arxiv.org/pdf/1604.03540.pdf>.

Smirnov, et al., "Hard Example Mining with Auxiliary Embeddings", Proceedings of the IEEE Conference on Computer Vision and Pattern Recognition Workshops, Jun. 2018, pp. 37-46, <https://www.researchgate.net/publication/328809263_Hard_Example_Mining_with_Auxiliary_Embeddings>.

Sukhbaatar, et al., "Training Convolutional Networks With Noisy Labels", Workshop Contribution at ICLR2015, Apr. 10, 2015, 11 pages, <arXiv preprint arXiv:1406.2080>.

Szegedy, et al., "Inception-v4, Inception-ResNet and the Impact of Residual Connections on Learning", Proceedings of the Thirty-First AAAI Conference on Arlilicial Intelligence (AAAI-17), 2017, pp. 4278-4284, <http://www.cs.cmu.edu/~jeanoh/16-785/papers/szegedy-aaai2017-inception-v4.pdf>.

Van Grinsven, et al., "Fast convolutional neural network training using selective data sampling: Application to hemorrhage detection in color fundus images", IEEE Transactions on Medical Imaging, vol. 35, Issue 5, May 2016, pp. 1273-1284, <https://ieeexplore.ieee.org/document/7401052>.

Veit, et al., "Learning from noisy large-scale datasets with minimal supervision", Proceedings of the IEEE Conference on Computer Vision and Pattern Recognition, Apr. 10, 2017, 9 pages, <https://arxiv.org/pdf/1701.01619.pdf>.

Xue, et al., "Robust Learning at Noisy Labeled Medical Images: Applied to Skin Lesion Classification", 2019 IEEE 16th International Symposium on Biomedical Imaging (ISBI 2019), Apr. 8-11, 2019, pp. 1280-1283, <https://ieeexplore.ieee.org/document/8759203>.

\* cited by examiner

NUMBER OF SAMPLES FOR MG MALIGNANCY CLASSIFICATION TASK

|  | IMAGES | NORMAL | BENIGN | MALIGNANT |
|---|---|---|---|---|
| TRAINING SET, NO BENIGN | 5029 | 3580 | 0 | 1449 |
| TRAINING SET, 10% BENIGN | 5532 | 3580 | 503 | 1449 |
| TRAINING SET, 25% BENIGN | 6286 | 3580 | 1257 | 1449 |
| EVALUATION SET | 6636 | 6500 | 100 | 36 |

NUMBER OF SAMPLES FOR BREAST DENSITY CLASSIFICATION TASK

|  | IMAGES | A | B | C | D |
|---|---|---|---|---|---|
| TRAINING SET, NO AC | 900 | 300 | 150 | 150 | 300 |
| TRAINING SET, 10% AC | 990 | 300 | 195 | 195 | 300 |
| TRAINING SET, 25% AC | 1150 | 300 | 275 | 275 | 300 |
| EVALUATION SET | 300 | 30 | 120 | 120 | 30 |

FIG. 8

| AUROC RESULTS OF FOCAL TRIM LOSS AND BASELINES | | | |
|---|---|---|---|
| | NO BENIGN | 10% BENIGN | 25% BENIGN |
| BASELINE | 0.761 | 0.735 | 0.760 |
| TRIM ALL | - | 0.75 | 0.766 |
| FOCAL TRIM LOSS | - | 0.758 | 0.792 |

FIG. 9

| AUROC RESULTS FOR THE BREAST DENSITY CLASSIFIER | | | |
|---|---|---|---|
| | NO AC | 10% AC | 25% AC |
| BASELINE | 0.921 | 0.904 | 0.919 |
| TRIM ALL | - | 0.930 | 0.915 |
| FOCAL TRIM LOSS | - | 0.934 | 0.929 |

FIG. 10

TRAINING MACHINE LEARNING MODELS TO EXCLUDE AMBIGUOUS DATA SAMPLES

BACKGROUND

The present invention relates generally to the field of training machine learning models, and more particularly to training machine learning models for medical image classification.

Machine learning (ML) is the study of computer algorithms which automatically improve through experience. It is typically viewed as a subset of artificial intelligence (AI). Machine learning algorithms typically construct a mathematical model based on sample data, sometimes known as "training data", in order to determine predictions or decisions without being specifically programmed to do so.

Loss is a value indicative of how inaccurate a ML model's prediction was on a single example. If the model's prediction is perfect, the loss value is zero; otherwise, the loss value is greater. The objective of training a model is to find a set of weights and biases that have as low of a loss value as possible, on average, across all examples. The batch size is a quantity of samples processed prior to updating the ML model. The number of epochs is the quantity of complete passes through the training data set.

SUMMARY

According to an aspect of the present invention, there is a method, computer program product and/or system that performs the following operations (not necessarily in the following order): (i) receiving a machine learning (ML) model trained on a training data set that includes at least one subclass of data samples where disagreement exists between manual annotations for the samples and a related externally grounded determination; (ii) determining a set of loss values for data samples of the training data set in an epoch of training the ML model; (iii) determining a loss threshold; and (iv) trimming at least one data sample belonging to the at least one of said subclass from the training data set based on the loss threshold and the loss value(s) of the set of loss values corresponding to the at least one data sample.

DETAILED DESCRIPTION

Some embodiments of the present invention are directed to techniques for training machine learning models for improved accuracy at classifying medical imaging data sets by trimming ambiguous samples from training data sets. In some embodiments, a machine learning model is trained using a data set, where a subset of the data set comprises data with a conflict between a first label based on an expert opinion and a second label based on a ground truth based on a medical examination. During some epochs of training the machine learning model, loss values for each data sample in the epoch are compared against a loss threshold, with data samples with corresponding loss values that exceed the loss threshold that also belong to the subclass trimmed from the data set for subsequent epochs of training. The loss threshold for the next epoch is then updated based on loss values of the trimmed data set.

This Detailed Description section is divided into the following subsections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be any thing made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
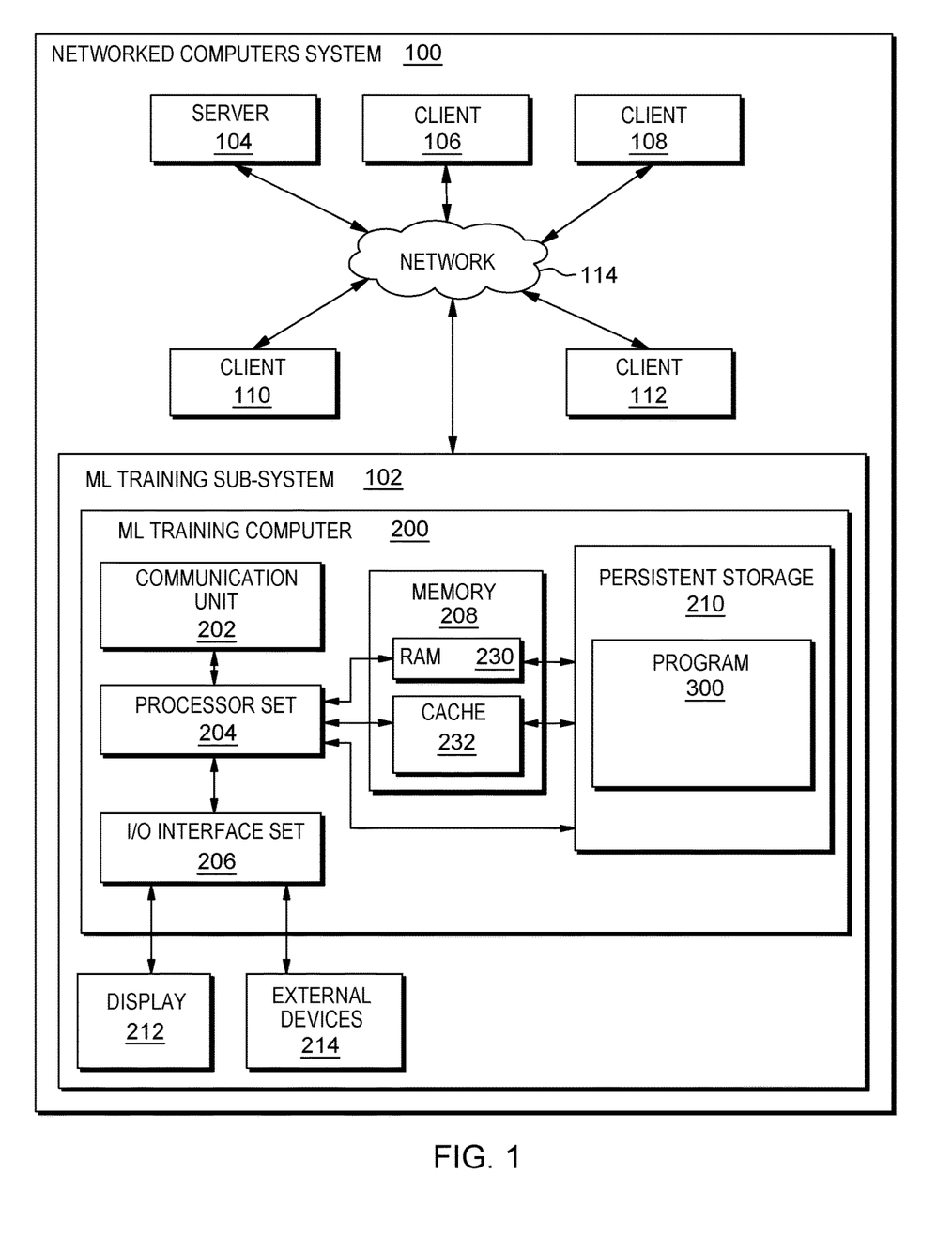
FIG. 1 is a block diagram view of a first embodiment of a system according to the present invention.

As shown in FIG. 1, networked computers system 100 is an embodiment of a hardware and software environment for use with various embodiments of the present invention. Networked computers system 100 includes: machine learning (ML) training subsystem 102 (sometimes herein referred to, more simply, as subsystem 102); client subsystems 104, 106, 108, 110, 112; and communication network 114. Subsystem 102 includes: ML training computer 200; communication unit 202; processor set 204; input/output (I/O) interface set 206; memory 208; persistent storage 210; display 212; external device(s) 214; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with ML training computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database).

In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
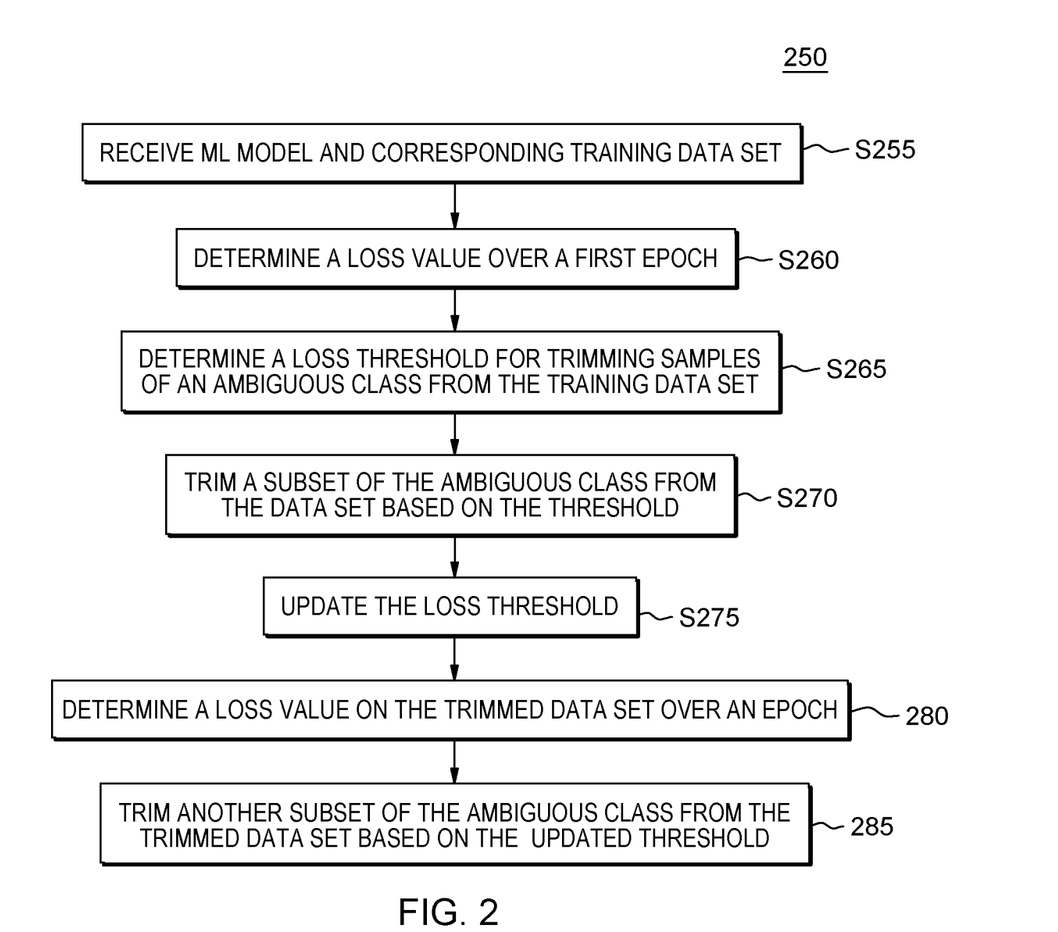
FIG. 2 is a flowchart showing a first embodiment method performed, at least in part, by the first embodiment system.
Figure 3:
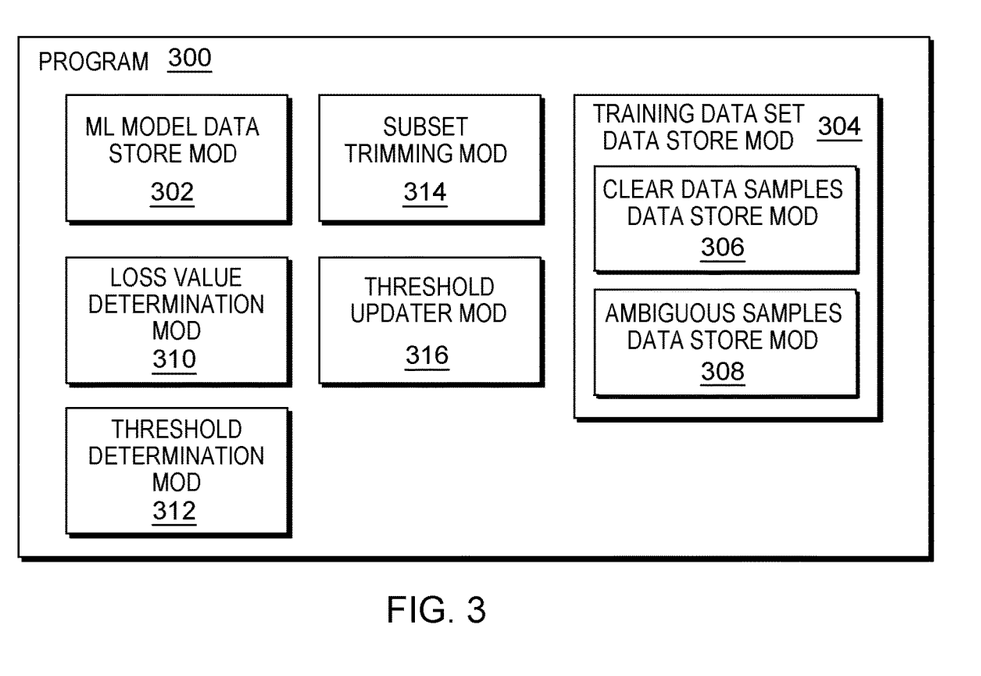
FIG. 3 is a block diagram showing a machine logic (for example, software) portion of the first embodiment system.
Figure 4:
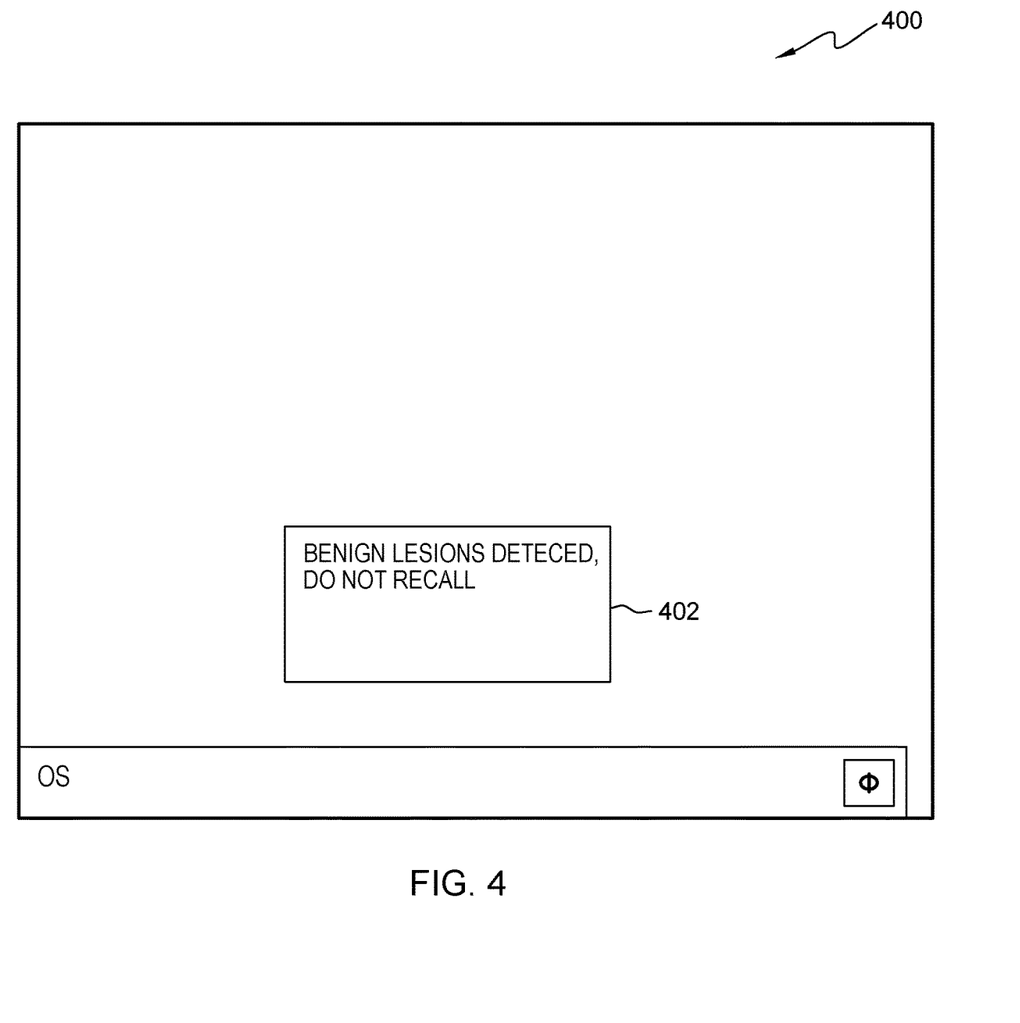
FIG. 4 is a screenshot view generated by the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or control performance of at least some of the method operations of flowchart 250. This method and associated software will now be discussed, over the course of the following paragraphs, with extensive reference to the blocks of FIGS. 1, 2 and 3.

Processing begins at operation S255, where machine learning (ML) model data store module ("mod") 302 receives a ML model and training data set data store mod 304 receives a corresponding training data set. The training data set and ML model are received from client 104 of FIG. 1 and are communicated over network 114 to subsystem 102. In this simplified embodiment, the training data set includes two subclasses of data samples: (i) clear data samples stored in clear data samples data store mod 306; and (ii) ambiguous data samples stored in ambiguous samples data store mod 308. An ambiguous data sample is a data sample with a manual annotation, usually determined by an expert, and a corresponding 'externally grounded determination,' also typically determined by an expert, where the annotation and the externally grounded determination disagree. An externally grounded determination is typically a conclusion or result determined by an expert concerning subject matter that is also the subject of the manual annotation but reached using different methodology that is more firmly grounded in directly observable evidence. For example, in this simplified embodiment, the training data set is a collection of four grayscale mammogram (MG) images, with manual annotations set by the radiologist who reviewed the MG images, and the externally grounded determination label (when present) set by the doctor who evaluated a biopsy sample from the patient subject of the MG image. A data sample will only have an externally grounded determination label when a biopsy is performed, which is typically only performed when the radiologist indicated a positive result in the MG image. By contrast, a data sample in the clear class either has no externally grounded determination or concurrence between the manual annotation and an externally grounded determination.

The first data sample image has an annotation of negative, meaning that the patient subject of the image was not sent for a biopsy, resulting in no externally grounded determination, making the first image a member of the clear class of data samples due to the absence of conflict between the manual annotation and an externally grounded determination. The second data sample image has an annotation of positive, and an externally grounded determination of a positive biopsy indicating malignancy. With concurrence between the manual annotation and the externally grounded determination, the second image belongs to the clear class of data samples. The third data sample image has an annotation of positive and an externally grounded determination of a negative biopsy indicative of a benign lesion. With disagreement between the manual annotation of the third image and the externally grounded determination of the third image, the third image belongs to the ambiguous class of data samples. The fourth data sample image has an annotation of positive and an externally grounded determination of a negative biopsy indicative of a benign lesion. Similarly, as with the third image, the fourth image also belongs to the ambiguous class of data samples. The ML model is trained to classify data sample MG images samples into one of two classes: (i) the image indicate a negative result, or an absence of cancer indicators; (ii) the image indicates a positive result, or the presence of cancer indicators. In alternative embodiments, a training data set includes a significantly larger number of data samples.

Processing proceeds to operation S260, where loss value determination mod 310 determines a loss value of a first epoch. In this simplified embodiment, the loss value is calculated using a cross-entropy function for each individual data sample. The first epoch includes all four data samples from the training data set. After the ML model classifies each data sample, the loss function returns a loss value indicative of the ML model's accuracy. In this simplified embodiment, the loss value for each data sample in this epoch is listed as follows: (i) the first data sample loss value is 2.3; (ii) the second data sample loss value is 4.5; (iii) the third data sample loss value is 3.6; and (iv) the fourth data sample loss value is 6.8.

Processing proceeds to operation S265, where threshold determination mod 312 determines a loss threshold for trimming samples of an ambiguous class from the training data set. In this simplified embodiment, the loss threshold is based on the average loss value determined at S260. The average of the loss values (2.3, 4.5, 3.6 and 6.8) is 4.3, which is the loss threshold. In alternative embodiments, other types of loss thresholds may be used. For example, the loss threshold can be another classifier trained to identify data samples belonging to the ambiguous class, or $E^k[L]/2$.

Processing proceeds to operation S270, where subset trimming mod 314 trims a subset of the ambiguous class from the data set based on the threshold. In this simplified embodiment, data samples of the ambiguous class with loss values above the loss threshold are trimmed from the training data set to create a trimmed data set. Two data samples are members of the ambiguous class: (i) the third data sample image; and (ii) the fourth data sample image. The loss value for the third data sample image, 3.6, is beneath the loss threshold, 4.3, so it is not trimmed from the training data set at this time. The loss value for the fourth data sample image, 6.8, is above the loss threshold, 4.3, so it is trimmed from the training data set at this time. The loss value for the second data sample image, 4.5, is above the loss threshold, 4.3, but it is not removed from the training data set because it does not belong to the ambiguous class. This data sample image is valuable in training the ML model towards improved accuracy in its classification tasks.

Processing proceeds to S275, where threshold updater mod 316 updates the loss threshold. In this simplified embodiment, the loss threshold is updated to be the average of the loss values from the first epoch of the data sample images, excluding any loss values corresponding to trimmed ambiguous class data sample images. At S270, the fourth data sample image was trimmed from the training data set, so the corresponding loss value is excluded from contributing to the updated loss threshold. With loss values from only the first data sample image (2.3), second data sample image (4.5), and third data sample image (3.6) remaining, the average loss value, and thus the updated loss threshold, is 3.5.

Processing proceeds to operation S280, where loss value determination mod 310 determines a loss value on the trimmed data set over an epoch. In this simplified embodiment, the loss value is again calculated using a cross-entropy function for each individual data sample. This epoch includes data sample images from the training data set, absent any data sample images from the ambiguous class previously excluded, resulting in only the first data sample image, second data sample image, and third data sample image included in the training data set for this epoch. After the ML model classifies each data sample image, the loss function returns a loss value indicative of the ML model's accuracy. In this simplified embodiment, the loss value for each data sample in this epoch is listed as follows: (i) the first data sample loss value is 1.9; (ii) the second data sample loss value is 4.0; and (iii) the third data sample loss value is 3.6.

Processing proceeds to operation S285, where subset trimming mod 314 trims another subset of the ambiguous class from the trimmed data set based on the updated threshold. In this simplified embodiment, the updated loss threshold, set at S275, is 3.5 Similar to S270, any training data set images in the trimmed training data set belonging to the ambiguous class with a loss value above the updated loss threshold are trimmed from the training data set, creating a second trimmed training data set. In this simplified embodiment, only one data sample image belonging to the ambiguous class, the third data sample image, remains in the trimmed training data set. The loss value in this epoch for the third data sample image is 3.6, which is above the updated loss threshold. Since the third training data sample image belongs to the ambiguous class, and has a loss value for this epoch above the previously updated loss threshold, it is trimmed from the training data set, resulting in a second trimmed training data set which includes only the first data sample and the second data sample.

Subsequent epochs, if desired, may begin after updating the threshold as in S275, then proceeding through S280 and S285. When the ambiguous class data samples have been sufficiently trimmed from the training data set, with a finally trimmed training data set remaining, the ML model may then perform epochs of training using the finally trimmed training data set. Trimming the ambiguous class data samples from the data set facilitates a more accurate machine learning model by virtue of the ambiguous class data samples introduce inaccuracy to the machine learning model.

III. Further Comments and/or Embodiments

Some embodiments of the present invention recognize the following facts, potential problems and/or potential areas for improvement with respect to the current state of the art: (i) deep neural networks rely on large amounts of data, some of which may be noisy or erroneous; (ii) for example, for supervised tasks this data is annotated by human experts, and as a result is prone to human error; (iii) in medical applications, images are often only one of the many modalities of data used for diagnosis; (iv) suspicious findings on images are often negated or confirmed on the basis of patient clinical condition and the results of other tests; (v) this amounts to a structural noise problem for medical image annotations; (vi) Medical imaging analysis is usually performed by a medical expert; (vii) for example, a radiologist will analyze a mammography image, or any other modality and produce an expert opinion; (viii) in cases where the expert believes that there is a medical condition, the patient is sent for further inspection; (ix) in mammography for example, the image is given a score; (x) if the score is high, the patient will be sent for a biopsy, where a final decision will be made; (xi) therefore, even instances where an expert has made mistakes, medical imaging pertaining to mammograms can still be categorized into 3 classes; (xii) the first, Negative (N)—where the expert thought the patient is healthy and she is indeed healthy; (xiii) the second, Positive (P)—where the expert thought the patient should go through further medical examination and she was indeed un-healthy; (xiv) the third, Undetermined (U)—where the expert thought the patient should go through further medical examination but she is healthy; (xv) this third category is elusive, since it is unclear whether the feature which indicates malignancy is indeed in the image; and (xvi) in some of the images it is present, and in some it is not.

Some embodiments of the present invention recognize the following facts, potential problems and/or potential areas for improvement with respect to the current state of the art: (i) the availability of enormous amounts of data and the constant improvement in computing power, have made deep-learning one of the most common machine learning techniques; (ii) given enough data, neural networks provide state-of-the-art results, and can easily outperform traditional computer-vision algorithms; (iii) however, network training relies on huge amounts of data to reach the levels of performance required; (iv) moreover, for fully supervised tasks all of this data must be annotated; (v) mammography (MG) is the primary imaging modality currently used as a screening tool to detect early breast cancer in women; (vi) the results of the examination are analyzed by a radiologist, and approximately 10% of the screening patients are sent for further medical examination; and (vii) the data from these examinations is one of the main sources being used to train deep learning networks to identify breast cancer.

Some embodiments of the present invention may include one, or more, of the following operations, features, characteristics and/or advantages: (i) a mechanism for removing undetermined images which harm deep neural network (DNN) training; (ii) taking a pretrained network on a dataset and continue fine-tuning it with the same dataset by removing images belonging to the undetermined class from training; (iii) training a DNN using a dataset containing the above three classes (P, N, and U); (iv) loading the model from stage 1, and according to some base rule relating to the loss of the training data continue training with the dataset P, N and a subset of U according to the rule; (v) updating the rule after each epoch/batch; (vi) one example rule is: all images above the average/median of the loss function calculated on the entire dataset; (vii) in an alternative embodiment, the rule can be a second network aimed at classifying images in the undetermined category; (viii) the special definition of the undetermined subclass; (ix) use loss value to determine exclusion from a training set; (x) use an online method; (xi) defining the ambiguous class (AC), and treating it separately during training; (xii) a technique for improving machine-learning model training by identifying a sub-class which is defined as all samples which have a disagreement between their manual annotation and an external ground truth relating to the sample, and removing this class during the training process; and (xiii) this technique includes: (a) calculating the loss value over one epoch, (b) determining a loss threshold in relation to the calculated loss, (c) any sample from the AC which has a value above the previously calculated threshold is ignored, and (d) at the end of an epoch update the loss threshold.

Some embodiments of the present invention may include one, or more, of the following operations, features, characteristics and/or advantages: (i) a novel training regime for classification tasks particularly effective for to the structure and challenges associated with medical imaging data; (ii) a mix of noisy loss trimming with hard examples mining; (iii) use the novel approach only on a subset of the data, defined as ambiguous; (iv) in one example, the ambiguous subset is defined as benign lesions; (v) this subset is: (a) confirmed by biopsy results, and (b) was sent for biopsy due to its unclear visual characteristic; (vi) hence the subset is treated as ambiguous; (vii) experimented on cancer classification for a dataset of breast mammography; (viii) in addition, there is another scenario where the ambiguous class appears in the breast tissue density classification task; (ix) this approach shows an improvement in classification performance compared to other state-of-the-art methods; (x) perform the technique on a distinct sub-class which is of special importance to the medical field; (xi) the identification of this sub-class is not trivial; and (xii) the threshold chosen for image selection is based on the loss statistics of the specific dataset instead of a constant percent of the images.

Figure 5:
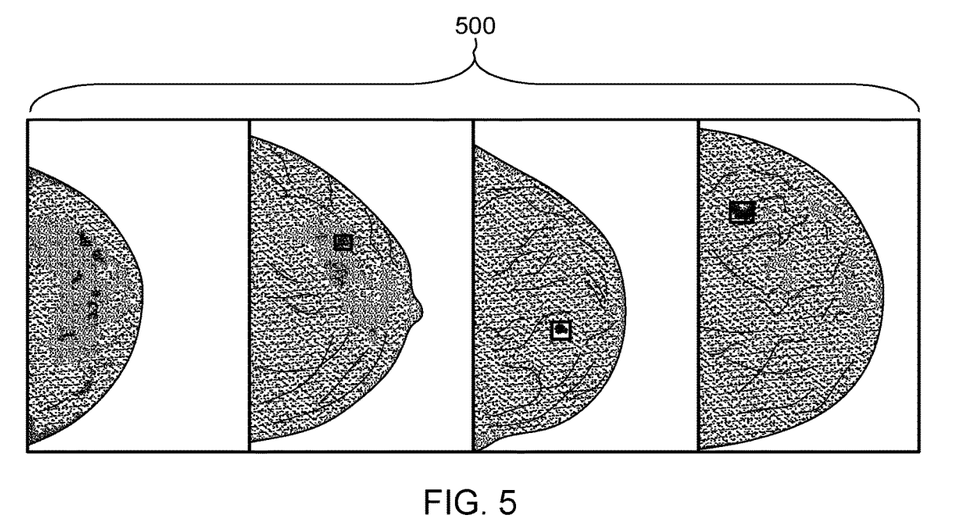
FIG. 5 is a screenshot view showing four example mammogram images corresponding to several subclasses of malignancy detection related images for a second embodiment.

Some embodiments of the present invention may include one, or more, of the following operations, features, characteristics and/or advantages: (i) annotations for MG datasets originate from two sources; (ii) human annotation based on images only; (iii) final results of further medical examination (for example, biopsy results); (iv) there is a unique subclass of breast MG imaging datasets that is defined as the ambiguous class (AC); (v) this subclass is characterized by the fact that its annotation label is based solely on the image, and differ from the final medical result; (vi) in the screening process, radiologists are required to mark each patient's study for recall or no recall; (vii) if a patient is recalled, but the biopsy results are benign, the radiologist's suspicion is refuted; (viii) for cancer detection in MG, the benign images where the radiologist marked the study for recall are identified as being ambiguous; (ix) FIG. 5 presents MG images 500 from three subclasses of the MG classification task—normal, benign (AC), and malignant; and (x) regarding FIG. 5, the findings have subtle differentiation, and annotation may be challenging even for expert radiologists.

Figure 6:
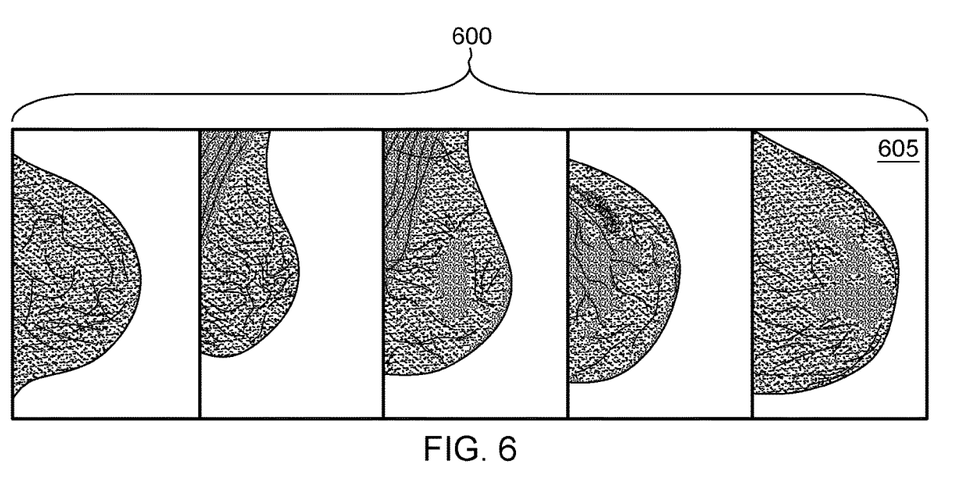
FIG. 6 is a screenshot view showing five example mammogram images corresponding to several subclasses of density related images for a third embodiment.

Some embodiments of the present invention may include one, or more, of the following operations, features, characteristics and/or advantages: (i) this AC can be identified in another use-case of MG analysis; (ii) for each MG analysis, the radiologist is also required to grade the density of the breast; (iii) breast density is categorized into four ranks: A, B, C, and D, where A is very low density, and D very high density; (iv) in this use-case there is no external ground truth (such as a biopsy confirming malignancy or benign status) and the rankings vary significantly between different experts; (v) due to the large disagreement, this technique was explored using a dataset that was annotated by five expert radiologists (each with at least five years of experience) and includes a report from the hospital where the exam was taken; (vi) We in this use-case scenario the AC is defined as the subset of the data where there is a disagreement between the report and the annotators; (vii) FIG. 6 presents MG images 600 from sub-classes of the MG breast density (BD) classification scenario—A, B, C, D; (viii) image number 605 is an example for the AC with disagreement between B and C sub-classes; (ix) the AC may be thought of as noise in the labels of the dataset, since some features that appear in the image may be misleading for the classification task; (x) there is no method for knowing in advance which of the images contain misleading images, and which do not; (xi) this noise can harm the training process and hence reduce the evaluation results of the underlying ML model; (xii) although this definition of AC does not fit the definition of flip-labels as it is not a-priori clear whether the relevant features for the classification task appear in the image; and (xiii) this approach distinguishes subclasses for loss evaluation purposes.

Some embodiments of the present invention may include one, or more, of the following operations, features, characteristics and/or advantages: (i) a novel approach for tackling the unique noise of the AC subset; (ii) this approach consists of dynamically removing training images that belong to the AC subclass; (iii) the images to be removed are chosen at the beginning of each epoch, and are chosen in relation to the statistics of the epoch loss; (iv) this approach is sensitive to the internal structure of the AC; (v) if all samples of the AC have a very low loss relative to the entire sample loss statistics, no image will be removed, while in other cases, a large portion may be removed; (vi) this approach can be shown through two different classification example tasks: (a) MG classification of malignant versus non-malignant where the AC is the benign class, and (b) MG classification of low breast density versus high breast density (A, B versus C, D) where the AC is the subset of the data in which there is disagreement between the annotators and the medical report; (vii) each of the example tasks use three training sets with an increasing amount of AC to fully explore the impact of this unique class on the prediction of the network; (viii) this novel approach shows superior results in comparison of using the entire training set; (ix) this novel approach exploits the gap between a patient diagnosis at the end of the diagnostic workup and the outcome of one specific examination done during this workup; (x) identifying the ambiguous subset, which can be relevant for general medical examinations tasks; (xi) creating a unique model for training that removes only ambiguous images; (xii) setting a dynamic threshold for selecting images to be removed; and (xiii) the threshold depends on the loss statistics of the entire dataset and is therefore sensitive to the internal structure of the AC.

Some embodiments of the present invention may include one, or more, of the following operations, features, characteristics and/or advantages: (i) one goal is to teach a classifier to capture the samples belonging to the AC and selectively ignore a sub-sample of them during training; (ii) this task is conceptually similar to other methods for trimming noisy labels, except that here there is a-priori knowledge about the dataset; (iii) this enables the ability to apply the trimming specifically to the unclear/ambiguous class, rather than trimming the full dataset, which may remove good samples from other classes; and (iv) this is one focus for the trim loss technique.

Some embodiments of the present invention leverage the following equations in executing focal trim loss according to the embodiments of the present invention:

Let $\{\mathcal{X}, \mathcal{Y}\}$ be a set of input image samples and their corresponding labels that some of which belong to an ambiguous class $C_{AC}$ and the rest to a clear class $C_{CL}$, such that: $\{x, y\} \in \{\mathcal{X}, \mathcal{Y}\} = \{\mathcal{X}_{C_{CL}}, \mathcal{Y}_{C_{CL}}\} \cup \{\mathcal{X}_{C_{AC}}, \mathcal{Y}_{C_{AC}}\}$. $\theta$ is defined as the model's parameters and $L_i(\theta)$ as the cross-entropy loss function on sample $i$..

Equation 1

$$L_K^{FT} = \frac{1}{\tilde{N}} \left( \sum_{i \in C_{CL}} L_i + \sum_{i \in C_{AC}} \chi_{\phi k}(L_i) \right) \quad (EQ.\ 1)$$

where $\chi_\phi(x)$ is defined as,

Equation 2

$$\chi_\phi(x) = \begin{cases} x, & x < \phi \\ 0, & \text{else} \end{cases}, \quad (EQ.\ 2)$$

and $\tilde{N}$ is the number of samples which were not removed in EQ. 1 due to EQ 2. The threshold $\phi_k$ is updated at the end of each epoch, and is dependent on the statistics of the loss of the previous epoch. The details of this dependency need to be set separately for each dataset, as the internal structure of the AC may vary.

Some embodiments of the present invention may include one, or more, of the following operations, features, characteristics and/or advantages: (i) for the medical image classification tasks, a customized Inception-ResNet-V2 architecture can be used; (ii) an example input to the network is a grayscale image resized to 1024×512; (iii) in some examples the network was composed of 14 Inception-Resnet blocks that are fed to a global max pooling (GMP) layer followed by two fully connected layers and a softmax layer; (iv) in some examples the CNN models are trained on an IBM PowerAI machine with Nvidia Tesla-V100-16G GPU; (v) also using an Adam optimizer with a learning rate of 10-4; (vi) an l2 regularization with a decay parameter of 10-4; (vii) the network converged after 60 epochs, which took approximately 1 day; (viii) the threshold selection was treated as a hyper-parameter that requires tuning; (ix) it was not a goal to remove a fixed number of samples, rather only those samples that deviate from the loss statistics; (x) hence, after parameter-tuning the threshold $\phi$ was set as $E^k [L]/2$; (xi) the training was done in two phases; (xii) first training the model with all the images until it converges and then trimming images; (xiii) since the trimming threshold is set relative to the average loss value, the first stage is needed for the loss values to stabilize; and (xiv) otherwise the images that were removed would not necessarily be the ones that harm the training.

Figure 7:
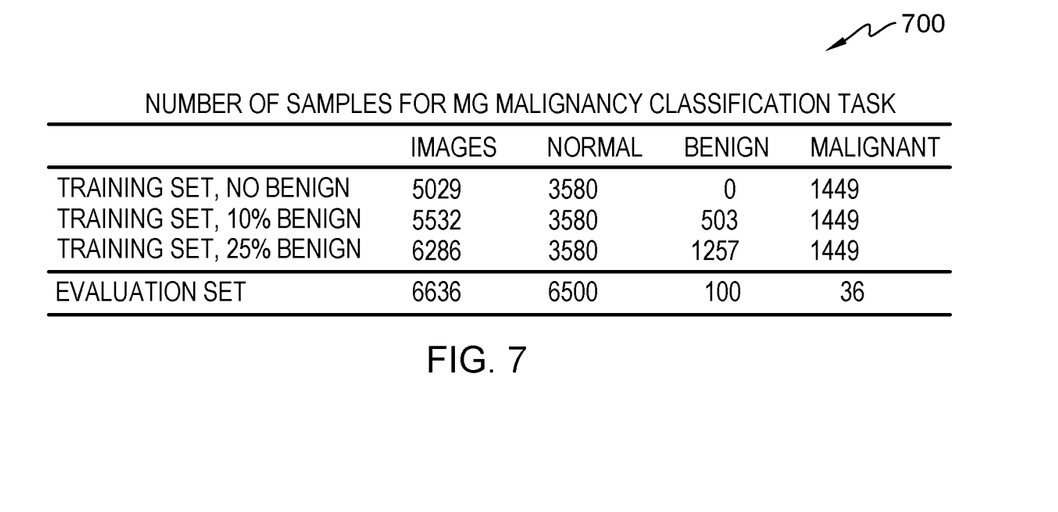
FIG. 7 is a table showing sample data sets used in an example of the second embodiment.
Figure 8:
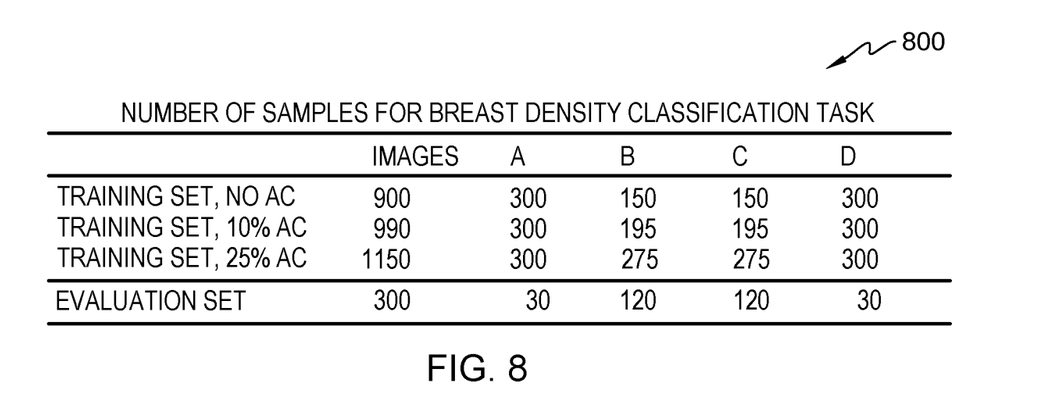
FIG. 8 is a table showing sample data sets used in an example of the third embodiment.

Some embodiments of the present invention may include one, or more, of the following operations, features, characteristics and/or advantages: (i) two different datasets for two different MG classification tasks: (a) malignancy, and (b) breast density; (ii) for the malignancy classification, the dataset consists of MG images from two private institutes; (iii) restricting the training dataset to one institute in order to avoid uncontrolled bias; (iv) the evaluation set was from the other institute; (v) its distribution was similar to that in the screening population; (vi) the ground truth label was based on the pathology report of the biopsied breasts; (vii) patients were labeled 'Positive' if their breast biopsy results was 'Malignant'; (viii) patients with 'Benign' breast biopsy results or with no biopsy were labeled as 'Negative'; (ix) the baseline training set consisted of 5029 mammogram images from 1633 patients with no benign lesions; (x) 80% of the samples were used in training; (xi) the other 20% were held out for validation; (xii) three datasets were used for training; (xiii) 10%, and 25% of benign images were added to the baseline data set to create the second and third datasets, where the 10% and 25% form the AC of those datasets; (xiv) the evaluation set contained 6636 mammogram images from 3975 patients; (xv) dataset distribution in the training and evaluation cohorts are given in table 700 of FIG. 7; (xvi) for the breast density classifier three different training sets are used with varying percentages of ambiguous samples; (xvii) the baseline set contained no ambiguous samples, with 10%, and 25% added to the second and third training sets respectively; (xviii) all of the resulting models were evaluated on a test set with a fixed density distribution; (xix) the ground truth was defined as the density value in the report for the training set and as the majority vote among the annotators for the test set; (xx) patients were labeled 'Low' if their breast density annotation was 'A' or 'B'; (xxi) patients with 'C' or 'D' breast density annotation were labeled as 'High'; and (xxii) an example of breast density data is summarized in table 800 of FIG. 8.

Figure 9:
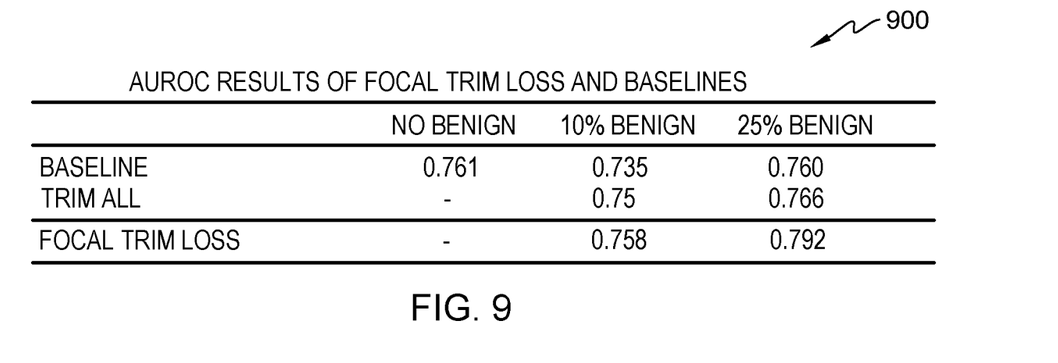
FIG. 9 is a table showing results comparing between the second embodiment and state of the art methods.

Some embodiments of the present invention may include one, or more, of the following operations, features, characteristics and/or advantages: (i) this approach contends that the AC is unique and should be trimmed separately; (ii) to quantify the impact of the Focal Trim Loss method, a classifier is trained to classify malignant versus non-malignant MG images; (iii) for this task, benign images are used as the AC; (iv) compare the results we obtained using different techniques; (v) a first technique is the Baseline classifier, which uses all training samples with no modifications; (vi) a second technique is a Trim all technique, which trims all images above a specific threshold; (vii) a third technique is the Focal trim loss, which only trims images belonging to the AC; (viii) the trim all and the focal trim loss techniques training were done in two phases according previously discussed methodology; (ix) to evaluate the focal trim loss technique, training sets with a growing number of benign samples were used; (x) the results are listed in Table 900 of FIG. 9; (xi) focal trim loss yields consistently better results than any of the other techniques; (xii) an average improvement of 3 points in Area Under the Receiver Operating Characteristics (AUROC) values relative to baseline training; (xiii) for the baseline classifier, adding benign samples to the training data set lead to an initial decrease in the results compared to no benign samples; (xiv) this result is counter intuitive since benign samples are part of the test set; (xv) nevertheless, this supports the assumption that samples from the benign class may harm the training process, and should be used with caution; and (xvi) using the trim all method, slightly improved AUROC results are observed compared to the baseline results and the No Benign set, but are still inferior to the focal trim loss technique.

Figure 10:
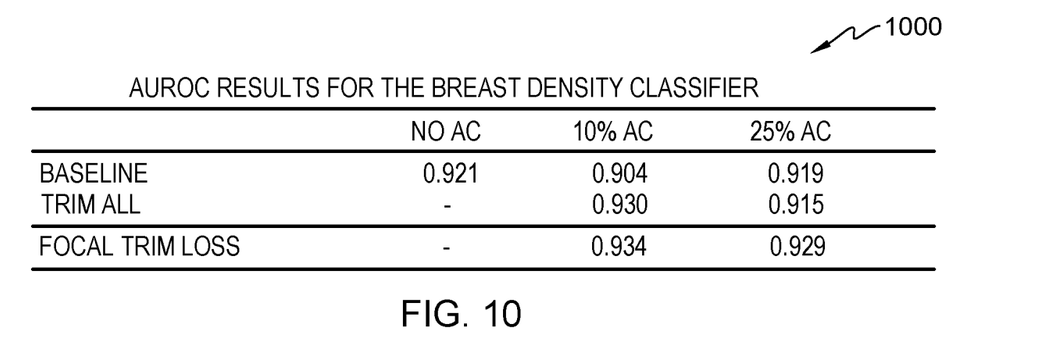
FIG. 10 is a table showing results comparing between the third embodiment and state of the art methods.

Some embodiments of the present invention may include one, or more, of the following operations, features, characteristics and/or advantages: (i) using our focal trim loss for other applications related to medical imaging; (ii) breast density classification is an interesting use-case where AC is useful, although it diverges from the original definition; (iii) training breast density classifiers with varying numbers of ambiguous cases as described in table 800 of FIG. 8; (iv) evaluated them on a test set following the population density distribution of (10%, 40%, 40%, 10%) for classes (A, B, C, D); (v) table 1000 of FIG. 10 shows consistently improved results when focal trim loss is applied to the ambiguous class compared to the baseline technique; (vi) the AC was defined as a conflict between an image label and the final result of the exam; (vii) this definition may be better refined through the integration of more medical information; and (viii) further extension of this refinement may lead to several sub-classes of the dataset with different treatments for each one.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

In an Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, and application-specific integrated circuit (ASIC) based devices.

Without substantial human intervention: a process that occurs automatically (often by operation of machine logic, such as software) with little or no human input; some examples that involve "no substantial human intervention" include: (i) computer is performing complex processing and a human switches the computer to an alternative power supply due to an outage of grid power so that processing continues uninterrupted; (ii) computer is about to perform resource intensive processing, and human confirms that the resource-intensive processing should indeed be undertaken (in this case, the process of confirmation, considered in isolation, is with substantial human intervention, but the resource intensive processing does not include any substantial human intervention, notwithstanding the simple yes-no style confirmation required to be made by a human); and (iii) using machine logic, a computer has made a weighty decision (for example, a decision to ground all airplanes in anticipation of bad weather), but, before implementing the weighty decision the computer must obtain simple yes-no style confirmation from a human source.

Automatically: without any human intervention.

What is claimed is:

1. A computer-implemented method (CIM) comprising:
receiving, by one or more processors, a machine learning (ML) model trained on a training data set, wherein the training data set includes at least one subclass of data samples where a disagreement exists between at least one manual annotation of a data sample and a related externally grounded determination;
determining, by the one or more processors, a loss value for each data sample of the training data set using a cross-entropy function;
determining, by the one or more processors, a loss threshold for trimming at least one data sample from the training data set; and
trimming, by the one or more processors, a first data sample with a first lost value above the loss threshold from the training data set to create a trimmed data set.

2. The CIM of claim 1, further comprising:
updating, by the one or more processors, the loss threshold based, at least in part, on a set of loss values and the trimmed data set.

3. The CIM of claim 2, further comprising:
training, by the one or more processors, the ML model through a plurality of epochs, where each epoch includes:
determining, by the one or more processors, a set of epoch loss values for data samples in the trimmed data set, and
trimming, by the one or more processors, at least one data sample belonging to the at least one subclass from the trimmed data set based on the updated loss threshold and the set of epoch loss values.

4. The CIM of claim 1, wherein the loss threshold is a second ML model trained to classify a plurality of images in the training data set into: (i) the at least one subclass of data samples where the disagreement exists between the at least one manual annotation of the data sample and the related externally grounded determination, or (ii) another subclass.

5. The CIM of claim 1, wherein:
the training data set is a plurality of mammogram (MG) images with corresponding labels comprising manual annotations indicating a presence or an absence of malignancy indicators in an image; and
the related externally grounded determination is one or more biopsy results indicating a presence or an absence of malignancy.

6. The CIM of claim 1, wherein:
the training data set is a plurality of mammogram (MG) images with corresponding labels comprising manual annotations indicating an average density of a tissue; and
the related externally grounded determination is a report of a physical examination performed with an exam that contributed to generation of the image.

7. A computer program product (CPP) comprising:
a machine readable storage device; and
computer code stored on the machine readable storage device, with the computer code including instructions for causing a processor(s) set to perform operations including the following:
receiving a machine learning (ML) model trained on a training data set, wherein the training data set includes at least one subclass of data samples where a disagreement exists between at least one manual annotation of a data sample and a related externally grounded determination;
determining a loss value for each data sample of the training data set using a cross-entropy function;
determining a loss threshold for trimming at least one data sample from the training data set; and
trimming a first data sample with a first lost value above the loss threshold from the training data set to create a trimmed data set.

8. The CPP of claim 7, wherein the computer code further includes instructions for causing the processor(s) set to perform the following operations:
updating the loss threshold based, at least in part, on a set of loss values and the trimmed data set.

9. The CPP of claim 8, wherein the computer code further includes instructions for causing the processor(s) set to perform the following operations:
training the ML model through a plurality of epochs, where each epoch includes:
determining a set of epoch loss values for data samples in the trimmed data set, and
trimming at least one data sample belonging to the at least one subclass from the trimmed data set based on the updated loss threshold and the set of epoch loss values.

10. The CPP of claim 7, wherein the loss threshold is a second ML model trained to classify a plurality of images in the training data set into: (i) the at least one subclass of data samples where the disagreement exists between the at least one manual annotation of the data sample and the related externally grounded determination, or (ii) another subclass.

11. The CPP of claim 7, wherein:
the training data set is a plurality of mammogram (MG) images with corresponding labels comprising manual annotations indicating a presence or an absence of malignancy indicators in an image; and
the related externally grounded determination is one or more biopsy results indicating a presence or an absence of malignancy.

12. The CPP of claim 7, wherein:
the training data set is a plurality of mammogram (MG) images with corresponding labels comprising manual annotations indicating an average density of a tissue; and
the related externally grounded determination is a report of a physical examination performed with an exam that contributed to generation of the image.

13. A computer system (CS) comprising:
a processor(s) set;
a machine readable storage device; and
computer code stored on the machine readable storage device, with the computer code including instructions for causing the processor(s) set to perform operations including the following:
receiving a machine learning (ML) model trained on a training data set, wherein the training data set includes at least one subclass of data samples where a disagreement exists between at least one manual annotation of a data sample and a related externally grounded determination;
determining a loss value for each data sample of the training data set using a cross-entropy function;

determining a loss threshold for trimming at least one data sample from the training data set; and trimming a first data sample with a first lost value above the loss threshold from the training data set to create a trimmed data set.

14. The CS of claim 13, wherein the computer code further includes instructions for causing the processor(s) set to perform the following operations:

updating the loss threshold based, at least in part, on a set of loss values and the trimmed data set.

15. The CS of claim 14, wherein the computer code further includes instructions for causing the processor(s) set to perform the following operations:

training the ML model through a plurality of epochs, where each epoch includes:
  determining a set of epoch loss values for data samples in the trimmed data set, and
  trimming at least one data sample belonging to the at least one subclass from the trimmed data set based on the updated loss threshold and the set of epoch loss values.

16. The CS of claim 13, wherein the loss threshold is a second ML model trained to classify a plurality of images in the training data set into: (i) the at least one subclass of data samples where the disagreement exists between the at least one manual annotation of the data sample and the related externally grounded determination, or (ii) another subclass.

17. The CS of claim 13, wherein:

the training data set is a plurality of mammogram (MG) images with corresponding labels comprising manual annotations indicating a presence or an absence of malignancy indicators in an image; and the related externally grounded determination is one or more biopsy results indicating a presence or an absence of malignancy.

18. The CS of claim 13, wherein:

the training data set is a plurality of mammogram (MG) images with corresponding labels comprising manual annotations indicating an average density of a tissue; and the related externally grounded determination is a report of a physical examination performed with an exam that contributed to generation of the image.

* * * * *